US012508013B2

(12) United States Patent
Kovacs

(10) Patent No.: US 12,508,013 B2
(45) Date of Patent: Dec. 30, 2025

(54) DROP ON CARRIAGE ASSEMBLY, SYSTEM, AND METHOD

(71) Applicant: INNOVATIVE MEDICAL PRODUCTS, INC., Plainville, CT (US)

(72) Inventor: Tamas Kovacs, Burlington, CT (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 326 days.

(21) Appl. No.: 18/448,408

(22) Filed: Aug. 11, 2023

(65) Prior Publication Data

US 2023/0380826 A1 Nov. 30, 2023

Related U.S. Application Data

(63) Continuation-in-part of application No. 18/341,856, filed on Jun. 27, 2023, now abandoned, which is a continuation of application No. 17/364,689, filed on Jun. 30, 2021, now Pat. No. 11,717,280.

(51) Int. Cl.
*A61B 90/57* (2016.01)
*A61B 17/02* (2006.01)

(52) U.S. Cl.
CPC .... *A61B 17/025* (2013.01); *A61B 2017/0268* (2013.01); *A61B 2560/0443* (2013.01)

(58) Field of Classification Search
CPC ............ A61B 90/57; A61B 2560/0443; A61B 17/025; A61B 2017/0268; A61G 13/101; A61G 13/1245; F16B 2200/40; F16B 2200/403
See application file for complete search history.

(56) References Cited

U.S. PATENT DOCUMENTS

2016/0296401 A1* 10/2016 Cole .................... A61F 5/3776

* cited by examiner

*Primary Examiner* — Samuel S Hanna
(74) *Attorney, Agent, or Firm* — Wasserbauer Law, LLC; Damian G. Wasserbauer, Esq.; Nicholas E. Blanton, Esq.

(57) ABSTRACT

The present invention relates to a carriage assembly and, more particularly, to a carriage apparatus, system, and method for coupling to a base plate and slidably holding a patient positioner, such as a distractor, at one or more angles with respect to an operating table. The carriage assembly may comprise a base, a jaw, and a fastener, which, when tightened, urges the jaw and base to clamp the rail of a baseplate, the baseplate being coupled to a side rail clamp via pins. Tapered openings in the carriage base may hold the patient positioner either vertically or at an angle with respect to the vertical. A secondary carriage may hold a boot configured to hold a foot. The carriages may be linearly translated to position the knee at a precise angles and provide enhanced structural stability.

5 Claims, 8 Drawing Sheets

DROP ON CARRIAGE ASSEMBLY, SYSTEM, AND METHOD

CROSS REFERENCE TO RELATED APPLICATION

This application is a continuation-in-part of, and claims priority to, co-pending U.S. Non-Provisional patent application Ser. No. 18/341,856, filed on Jun. 27, 2023, entitled "Modular Distractor Apparatus, System, and Method", which is a continuation of U.S. Pat. No. 11,717,280, issued on Aug. 8, 2023, application Ser. No. 17/364,689, filed on Jun. 30, 2021, entitled "Modular Distractor Apparatus, System, and Method".

FIELD OF THE INVENTION

The present invention relates generally to patient positioning systems for surgical applications, and more particularly, to a carriage apparatus, system, and method for coupling to a base plate capable of slidably translating therealong, the carriage configured to hold a limb positioner or distractor at a desired position relative to an operating table.

BACKGROUND OF THE INVENTION

Surgical procedures increasingly require precise and predictable positioning of the joint, limb, or other body part corresponding to the surgical site. Optimal positioning requires a large range of easily available positive positioning adjustments, so that the limb, joint, or other body part can be precisely positioned and thereafter maintained in that desired position. First, specialized surgical procedure operating room (OR) or other support tables have been developed for precision positioning of the body part, but these specialized OR tables are generally useful for a limited type of surgeries, are expensive, and take up a lot of room. It would be desirable to have a patient positioning system, such as for knee replacement surgeries, that couples to a standard OR table with side rail. Second, it would be desirable to have a patient positioning systems that couple to a standard OR table with side rail wherein the system does not obstruct access by the surgeon to the surgical site. Third, it is desirable to have a patient positioning device that maintains a desired position throughout the surgery, without slipping, loosening, or otherwise moving during the procedure.

Consequently, there is a need for a patient positioning system that couples to OR tables having standard side rails, that is out of the surgeon's way, and that has improved holding characteristics.

SUMMARY OF THE INVENTION

The present invention advantageously fills the aforementioned deficiencies by providing a carriage capable of slidably coupling a patient positioning device, such as a distractor, to a base plate for use in knee replacement surgeries and other surgical procedures.

It is an object of the present invention to provide a carriage configured to couple a patient positioning device to a base plate, wherein the carriage, patient positioning device, etc., is capable of coupling to a standard OR table, such as an OR table including a side rail having industry-standard cross-sectional dimensions.

It is an object of the present invention to provide a carriage configured to couple a patient positioning device to a base plate, wherein the carriage, patient positioning device, etc., is positioned underneath or substantially underneath, the patient and/or surgical site, thereby reducing obstruction of the system and providing greater access for the surgeon and/or operating room personnel.

It is also an object of the present invention to provide a distractor that is mechanically decoupled from a patient positioning boot and/or boot carriage, wherein, for example, the carriage couples the distractor to the base plate, the distractor being located at a first position of a track of the base plate, and the patient positioning boot is coupled to a different carriage, the boot being located at a second position of the track. In this example, the carriage according to the present invention reflects an independent anchoring point, which may advantageously provide additional support, rigidity, and/or enhanced holding of the patient throughout the surgical procedure. Such support may be favorable for surgical applications requiring or benefiting from a high degree of stability, such as robotic surgical applications. Such a system may effectively form a triangle shape, a shape which is commonly known to enhance structural stability, the side of the triangle being formed by (i) a baseplate coupled to the OR table surface, (ii) a distractor disposed upwardly from the OR table surface from a dedicated carriage, and (iii) the lower leg of a patient, i.e., tibia/fibula, wherein the patient foot is coupled to a boot, the boot being coupled to the baseplate via a separate dedicated carriage.

It is an object of the present invention to provide a carriage configured to dispose the patient positioning device at a plurality of angles relative to the surface of the operating room table, for providing improved holding and/or positioning of the patient during surgery. One such advantage corresponds to overweight or obese patients for whom maintaining the femur in an orthonormal position relative to the OR table surface is not possible. Therefore, providing a carriage having a lateral offset angle $\beta$, such as an angle $\beta=15$ degrees, may effectively orient the leg of the patient so that the surgical procedure can be performed.

It is also an object of the present invention to provide a drop-on carriage, i.e., a carriage capable of connecting to a baseplate at a location between the ends of the track, such as along the length of the baseplate track. As compared to a clamp and/or carriage that is only capable of coupled to a track of a baseplate from either end, the drop on carriage advantageously can be added and/or removed from the surgical patient positioning system as desired by the surgeon. In one aspect, removal of the distractor and a corresponding low-profile, drop-on carriage from the patient positioning system, allows the surgeon to test the knee replacement, wherein the leg is full extended and laid flat on the table and/or baseplate or track. It may then be desirable to reestablish the initial surgical position with the knee being bent in the aforementioned triangle position, for further surgical correction of the knee replacement.

It is also an object of the present invention to provide a carriage configured to couple to a support platform or base plate, wherein the base plate may be clamped to the side rail of an operating table. In one or more embodiments, the carriage may be configured to hold a distractor apparatus for supporting and distracting the knee joint. Additional components may be coupled to the base plate and disposed proximate the carriage along another portion of the track of the baseplate, such as a boot, which may also be clamped to and/or translated linearly along the length of the base plate. As another example, one or more retractor clamps may be clamped to, and/or translated along, the base plate, wherein the retractor clamp may be configured to support a retractor system. Advantageously, the carriage according to the present invention may be shaped having a low profile, or otherwise shaped to be employed with any additional components, such that during repositioning, all components may move in concert, allowing for small adjustments to the angle of the knee changes. This may facilitate 'free flow' of the surgical procedure from one step to the next, with minimal time in between to reduce the total amount of time required, increase accuracy of the surgical procedure, and/or increase effectiveness of the patient positioning system.

Other desirable features and characteristics including will become apparent from the subsequent detailed description, the drawings, and the appended claims, when considered in view of this summary.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present disclosure, reference will be made to the following Detailed Description, which is to be read in association with the accompanying drawings, which are incorporated in and constitute a part of this specification, show certain aspects of the subject matter disclosed herein and, together with the description, help explain some of the principles associated with the disclosed implementations, wherein.

DETAILED DESCRIPTION

Figure 1:
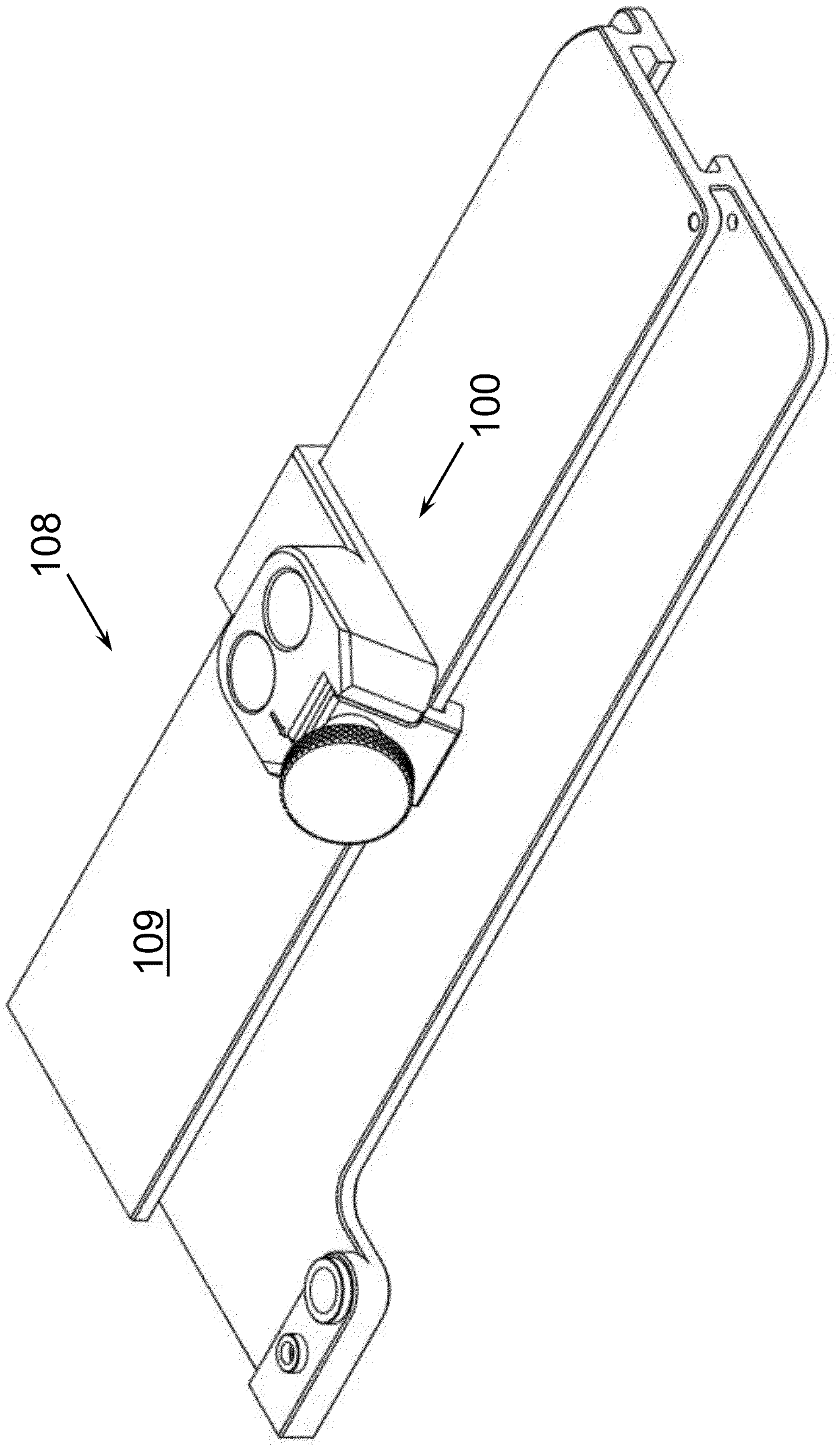
FIG. 1 illustrates a carriage slidably coupled to a base plate, according to an embodiment of the invention.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention. For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

FIGS. 1-8 illustrate certain embodiments and features generally shown as carriage apparatus, system, and method 100, according to the present invention. The carriage 100 may be employed as a component of a patient positioning system for surgical application; however, use of the carriage 100 is nonlimiting. Carriage 100 may be useful for a variety of applications, such as in the manufacturing industry, and other fields of use. For example, carriage 100 may be employed to secure and hold a work tablet or electronic device to a structure, for ease of use and display while in the field. Therefore, the applications of the carriage 100 shall be considered nonlimiting.

According to the present invention, carriage 100 may be generally adapted to couple a distractor 120 to a baseplate 108, which may be useful for knee replacement surgeries, or other surgeries, as shown in FIGS. 1, 6, 7A-7B, and 8. Baseplate 108 may be a separable baseplate 108, such as that disclosed by the applicant in U.S. Pat. Pub. No. 2022/273, 512, entitled Split Base Plate Assembly Using Pins, which is incorporated herein by reference in its entirety. Such a baseplate system may be used to provide a track portion 109 extending outwardly and/or upwardly from an operating room (OR) table or other support 101, and adapted for receiving and coupling to carriage 100. The carriage 100 may then advantageously be dropped on and coupled to the base plate 108 along any portion of track 109 and, for example, translated therealong to a desired position. The carriage 100 may be further configured to hold a patient positioner for a limb, such as a distractor 120 adapted to receive, hold, and/or distract a joint of, a lower limb of a patient. The carriage 100 may advantageously provide an attachment surface upon which the distractor 120 may be disposed at one or more angles.

Figure 2:
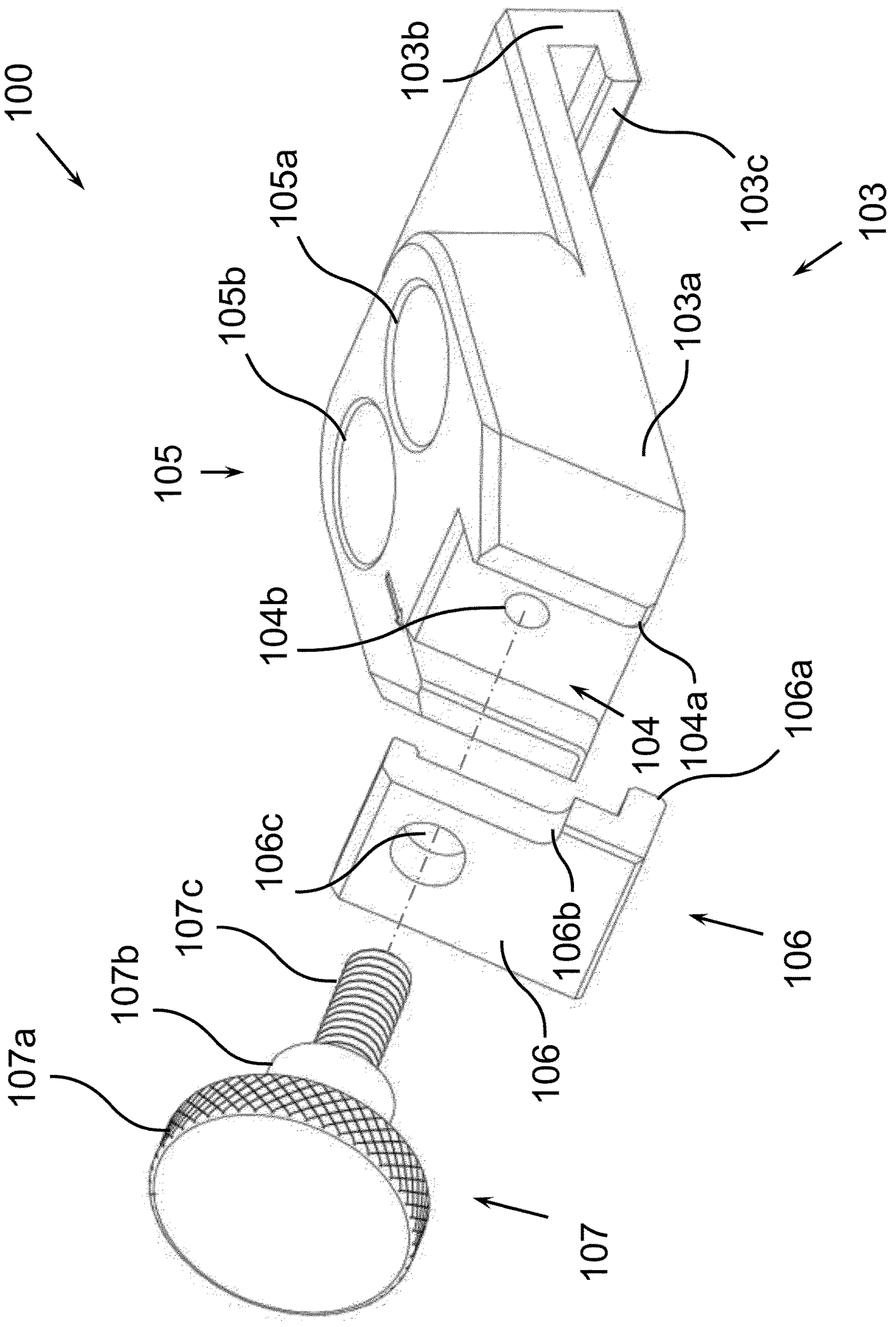
FIG. 2 illustrates an exploded, top, front, right-side perspective view of a carriage, according to an embodiment of the invention.
Figure 3:
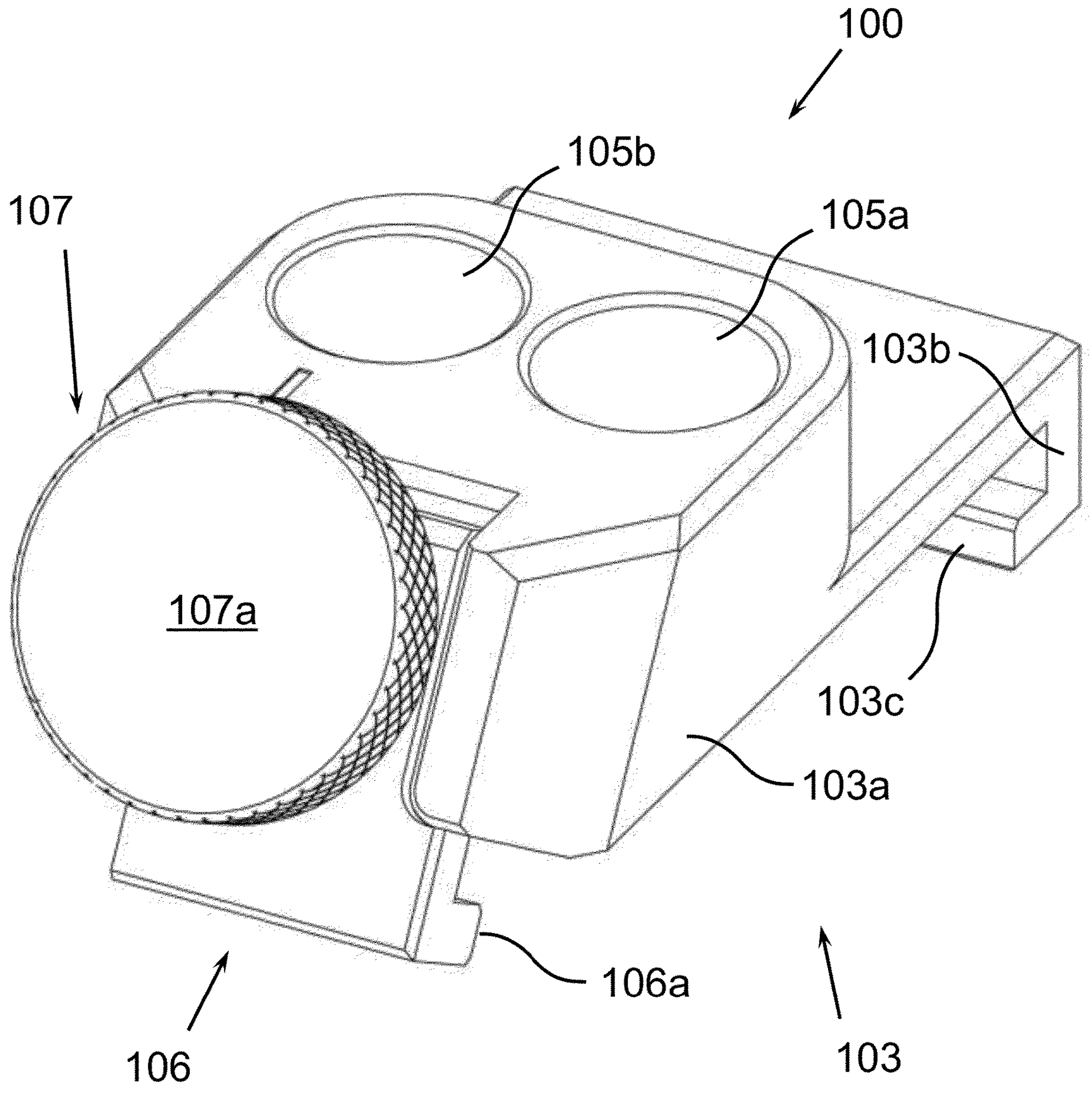
FIG. 3 illustrates a top, front, right-side perspective view of an assembled carriage, according to an embodiment of the invention.
Figure 4:
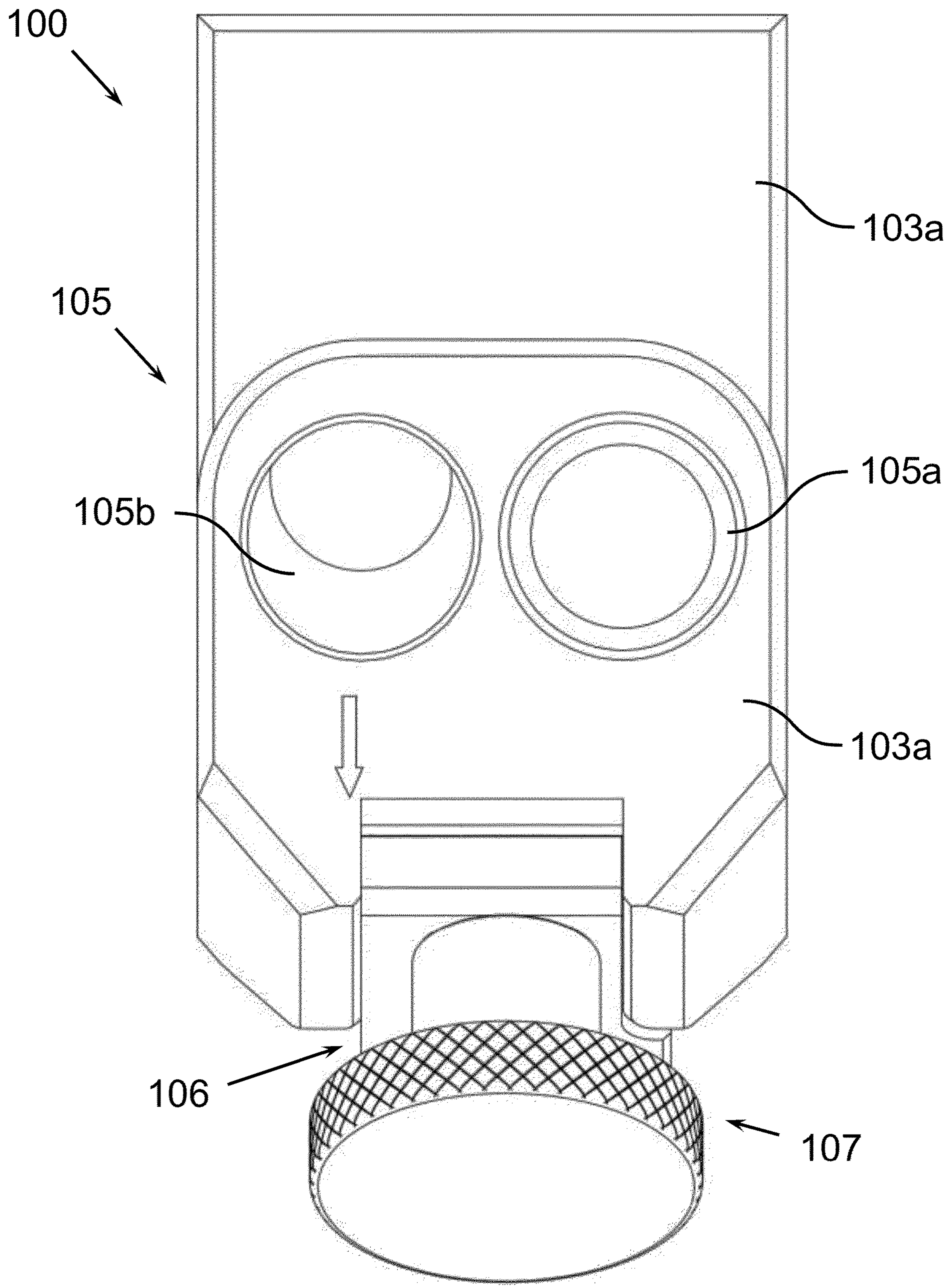
FIG. 4 illustrates a top view of a carriage, according to an embodiment of the invention.

FIGS. 2-4 illustrate an exploded view according to the present invention, wherein the carriage 100 may comprise a carriage body 103, a jaw 106, and a fastener assembly 107. The carriage 100 may include a carriage body 103, a slot portion 104, and one or more openings 105. Carriage body 103 may include a base 103*a*, a receiver portion 103*b*, a flange portion 103*c*, a slot portion 104, and one or more openings 105. Receiver portion 103*b* extends outwardly from the base 103*a*, and in coordination with flange portion 103*c*, receiver portion 103*b*, the underside of carriage body 103, and jaw 106, provides a C-shaped clamping assembly to fixedly couple the carriage to the baseplate 108 via track 109. Slot portion 104 of carriage body 103 may include chamfer 104*a* and an opening 104*b*. Slot portion 104 may be generally recessed, or otherwise configured to receive jaw 106. One or more openings 105 may be openings 105*a* and 105*b*, wherein such openings 105 may be configured to receive a tapered end 111 of an adapter 110 of distractor assembly 120, or other positioner, assembly, etc. Each opening 105*a*, 105*b* of the one or more openings 105 may be configured to dispose the distractor 120 at a distinct angle, as may be observed from FIG. 3. The first angle for example, corresponding to a first opening 105*a*, may be normal to, i.e., 90° the OR table 101 via a similarly-positioned track 109 of baseplate 108, when carriage 100 is employed and/or in operation. The second angle, for example, corresponding to a second opening 105*b*, may be disposed at any angle, such as an acute angle as measured from the normal of the upper surface of base 103*a*, or the normal defined by the upper surface of the track 109 of baseplate 108, and/or the normal defined by the surface of the OR table 101.

As shown in FIGS. 1-4 and 6-8, according to the present invention, jaw 106 may be held in a slot 104 of the carriage body 103 and secured thereto via operation of the fastener assembly 107. The jaw 106 further comprises a jaw flange 106*a* configured to engage a side of the track 109 of baseplate 108. Fastener assembly 107 may include a knurled portion 107*a*, a neck portion 107*b*, and a threaded portion 107*c*. In operation, the knurled portion 107*a* may be acted upon to advance the threaded portion 107*c* into opening 104*b*. Via a slight advancement into opening 104*b* of fastener assembly 107, the jaw 106 may be moveable, such as in a moveable jogging manner, wherein the jaw key 106*c* may be obround to accommodate such movement. This feature of jaw key 106*c* facilitates reorienting of the jaw 108 about track 109 in a manner that improves positioning to provide for effective clamping, repositioning, and the like. For example, upon clockwise turning of the fastener assembly 107, the jaw 106 may be loosely urged toward the base 103*a*, and upon subsequent tightening of the fastener assembly 107, neck 107*b* and slot 104 may rigidly position jaw 106 around the rail 109 of the base plate 108 to achieve effective clamping.

Referring to FIGS. 2-4, because it is desirable that the carriage 100 be sterilized prior to use in surgical applications, carriage 100 is configured for disassembly so that reentrant surfaces are reduced or eliminated. Reentrant surfaces may retain non-sterile matter that may affect the subsequent surgical use. Therefore, when carriage 100 is disassembled prior to sterilization, and then reassembled prior to use, it may be advantageous to have mechanical datums that prevent improper assembly. The jaw 106, in particular, may be subject to upside-down or reverse assembly. To prevent mis-assembly, one or more datums may be machined into the jaw 106 and/or slot 104 of the base 103*a*. In addition, the threaded opening 104*b* within the slot 104 may be offset toward the right side of the base 101. If improperly oriented, the holes on the base 104*b* and jaw 106*c* may not line up. Alternatively, other matching keys may be disposed in the slot 104 and jaw 106, without limitation, such that proper assembly may be ensured. In another aspect, certain opening may be through-holes within base 103*a*. For example, the one or more openings 105, such as openings 105*a* and 105*b* may be through holes. Similarly, opening 104*b* of slot portion 104 may be a through hole. This may aid sterilization.

Figure 5:
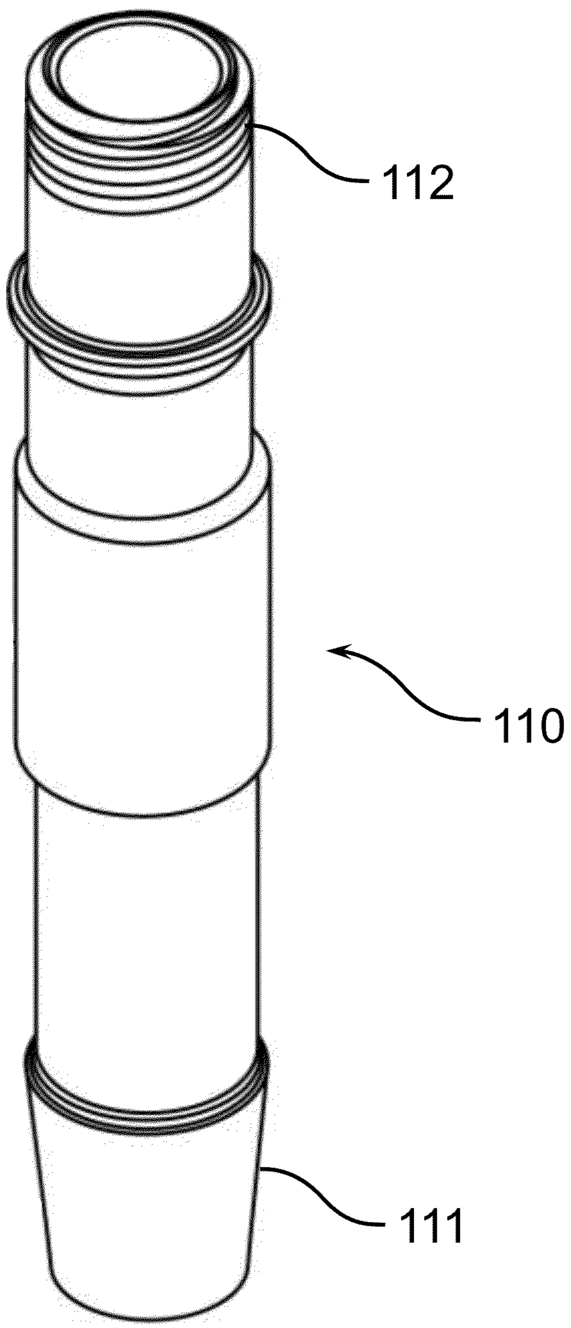
FIG. 5 illustrates a perspective view of an adapter, according to an embodiment of the invention.
Figure 6:
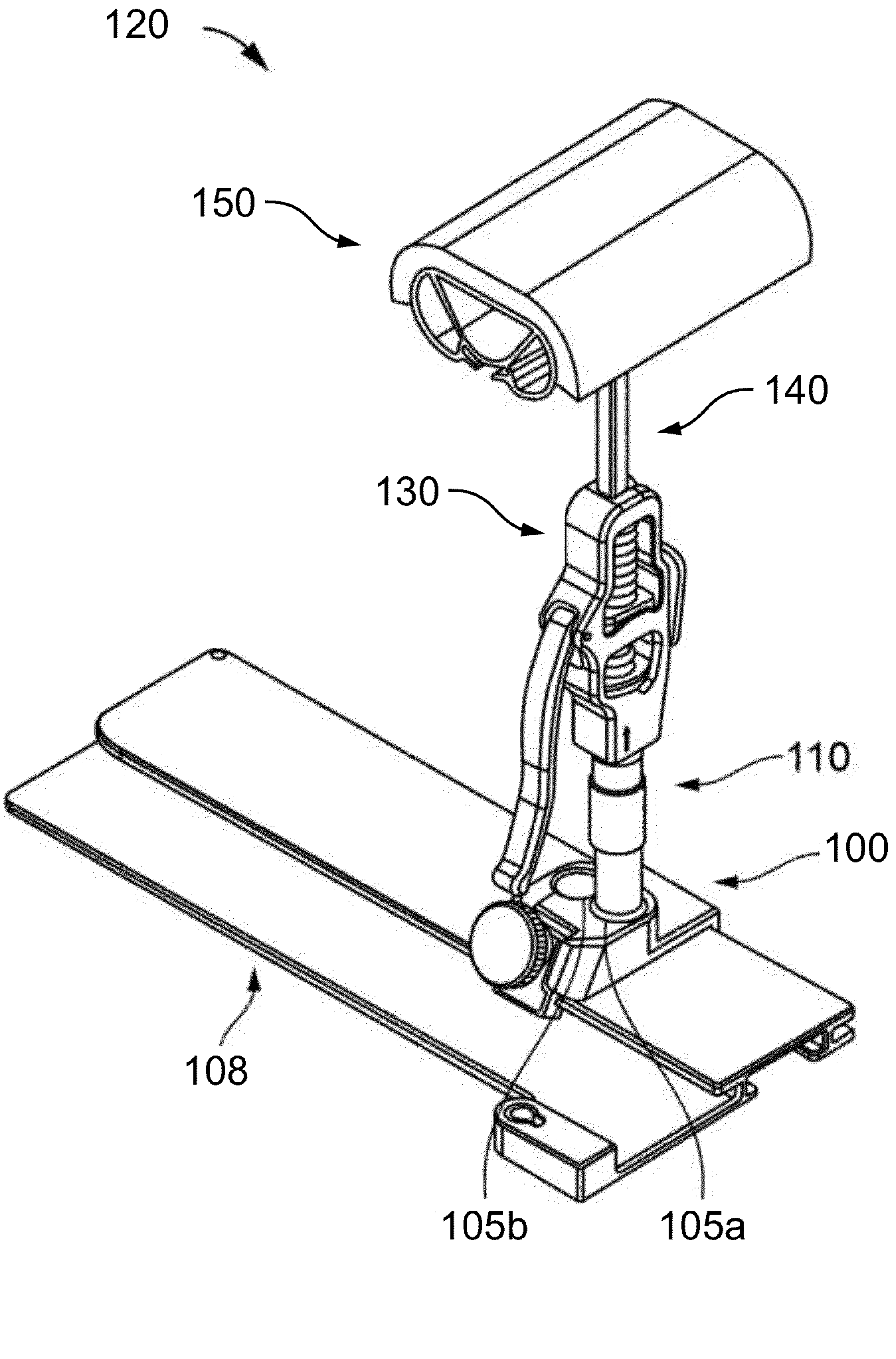
FIG. 6 illustrates a top, front, right-side perspective view of a carriage coupled to a base plate with a distractor coupled in an orthonormal orientation thereto, according to an embodiment of the invention.
Figure 7A:
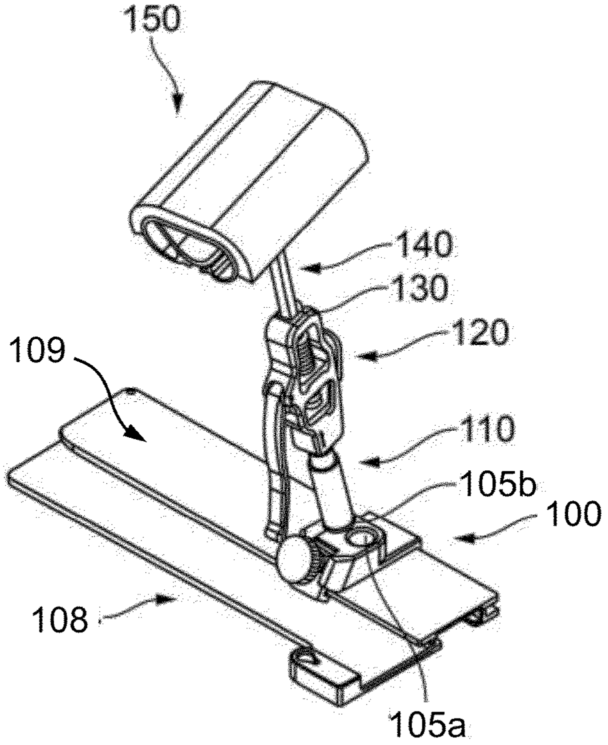
FIG. 7A illustrates a top, front, right-side perspective view of a carriage coupled to a base plate with a distractor coupled in an angled orientation thereto, according to an embodiment of the invention.
Figure 7B:
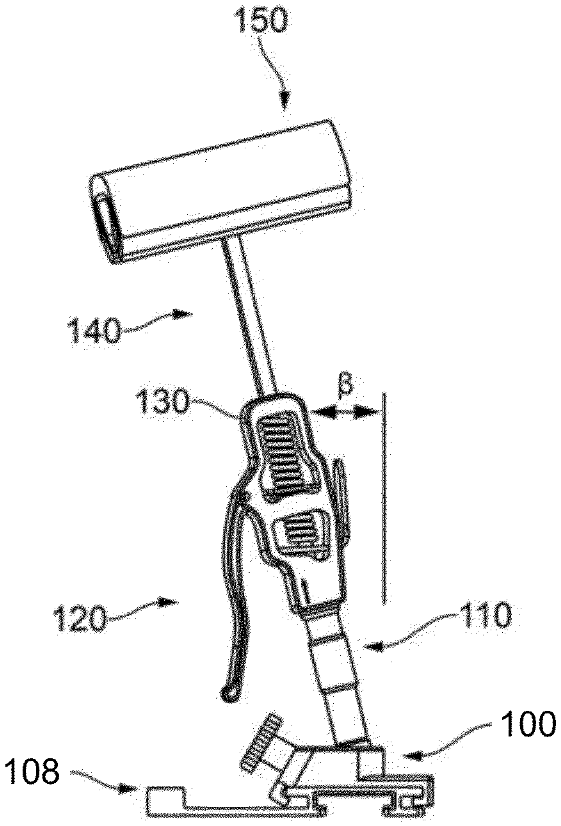
FIG. 7B illustrates a right-side view of a carriage coupled to a base plate with a distractor coupled in an angled orientation thereto, according to an embodiment of the invention.
Figure 8:
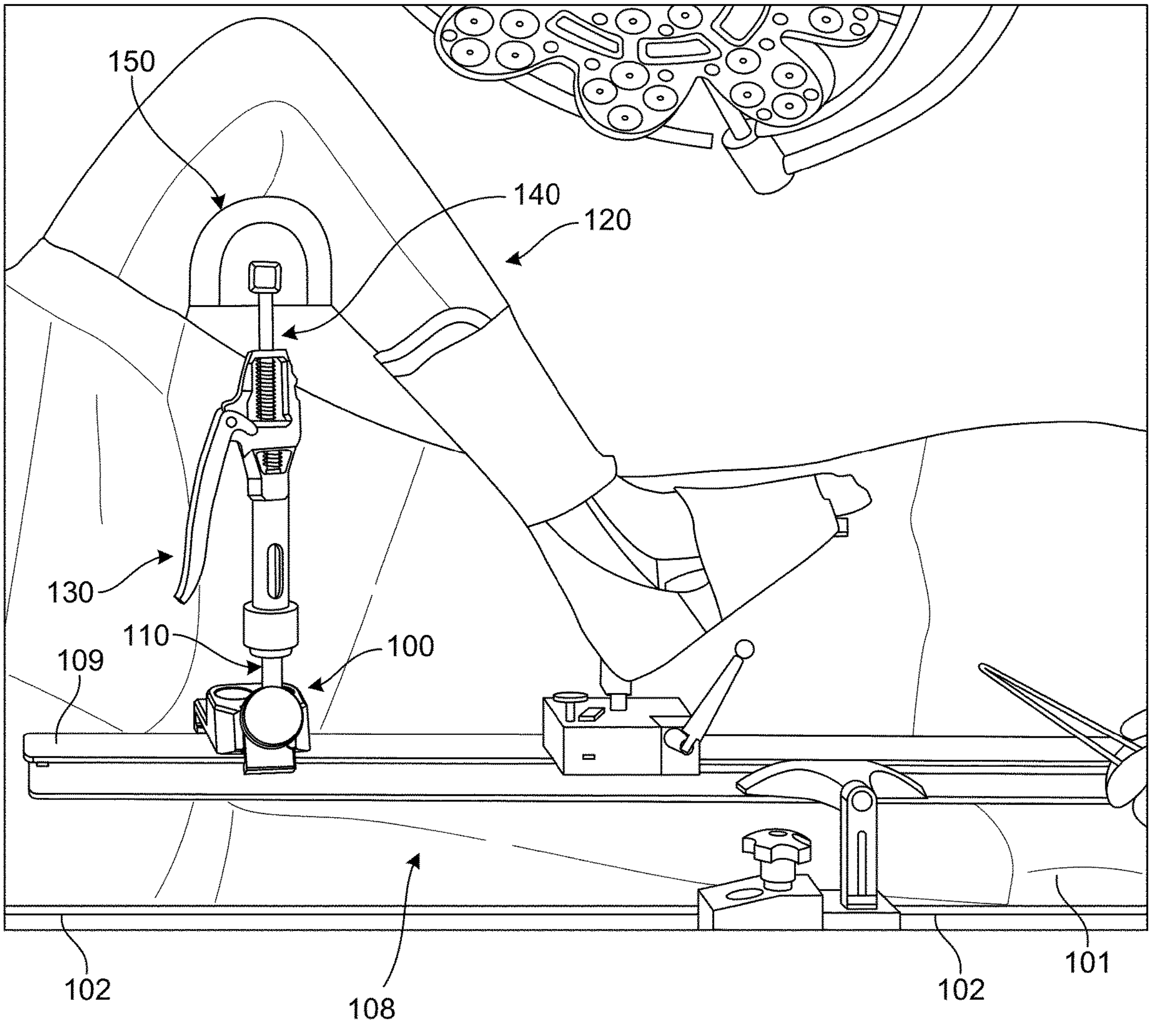
FIG. 8 illustrates an environmental view of a patient positioning system including a carriage, the system employed for a knee replacement surgery, according to an embodiment of the present invention.

Turning now to FIG. 5, an adapter 110 is shown that is configured to be received by one of the one or more openings 105*a*, 105*b* formed in the base 103*a*. The adapter 110 may have a generally cylindrical shape. Alternatively, the adapter 110 may have other cross-sectional profiles, such as square, rectangular, oval, star-shaped, or keyed, among others. One end of the adapter 110 may be a taper end 111 with an angle that is complementary to that of the openings 105*a*, 105*b* in the base 103*a* such that when adapter 110 is disposed in one or more openings 105, distractor 120 may rigidly couple to carriage 100. The attachment of distractor 120 to carriage 100 via tapered end 111 may be facilitated by gravity or other external forces, such as advancement of the distractor 120 against another object, or some combination thereof. As previously mentioned, the adapter 110 may be configured to couple to a variety of devices, such as positioners, distractors, or retractors, at a distal end 112. In the embodiment shown in FIG. 5, distal end 112 includes a threaded portion, but one skilled in the art will appreciate that other removable coupling methods may be used, such as, for example, via a set screw.

FIGS. 6, 7A-7B, and 8 illustrate the use of the carriage 100 being employed in the environment of a base plate 108 and a modular distractor 120, wherein the base plate 108 may be configured to be disposed on a surface of an OR table 101. The modular distractor 120 may comprise an adapter 110, a housing 130, a driver 140, and a positioner pad 150. The modular distractor 120 may be disposed vertically, i.e., coupled to carriage 100 via opening 105*a*. In certain embodiments employed for certain uses, opening 105*a* may be purposed for advancing positioner pad 150 upwardly against a patient joint, such as the underside of the knee. This orthonormal orientation relative to the upper surface of the OR table 101 and/or the track 109 of baseplate 108 ensure proper distraction of the joint as may be desired during surgery, because it represents a stable and surgically operable configuration thereof. Alternative angles may be employed, and are generally represented as opening 105*b*. As visible in FIG. 7B, angle β of opening 105*b*, represents the rigidly coupled positioning of distractor 120 relative to the OR table 101 and or the track 109 of base plate 108. For overweight patients for whom maintaining an orthonormal position of the leg may be difficult or impossible to achieve, such an angled orientation, as reflected by angle β of opening 105*b*, may provide an effective solution. In some embodiments, angle β of opening 105*b* may be formed ranging between 5° and 30°. Angle β of opening 105*b* may more preferably be formed ranging between 10° and 20°. In a preferred embodiment, angle β of opening 105*b* may be 15°, although other angles β may be selected and fall within the scope of this disclosure.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A carriage assembly for securely coupling a surgical joint distractor to the track of a baseplate, the carriage assembly comprising:

a base including a receiver portion extending outwardly from said base, a carriage flange disposed at an end of said receiver portion, a plurality of tapered openings formed within a top surface of said base, and a slotted portion having a slot opening, wherein a first tapered opening of said plurality of tapered openings is disposed at an orthonormal angle with respect to said top surface, and wherein a second tapered opening of said plurality of tapered openings is disposed at an acute angle with respect to the normal of said top surface;

a jaw including a jaw flange and a jaw opening; and a fastener assembly including a threaded portion;

wherein, in an assembled configuration, the fastener assembly extends through said jaw opening so that said threaded portion operably couples to said slot flange, so that advancing said fastener assembly urges the jaw flange toward the carriage flange, thereby securely coupling said carriage assembly to said track, and wherein said plurality of tapered openings are configured to receive said distractor.

2. The carriage assembly of claim 1 wherein said second opening of the plurality of openings is disposed at an angle of ranging between about 5 and about 30 degrees with respect to the normal of said top surface.

3. The carriage assembly of claim 1 wherein said second opening of the plurality of openings is disposed at an angle of 15 degrees with respect to the normal of said top surface.

4. The carriage assembly of claim 1, wherein said slot further comprises a recess formed in said base, said jaw configured to operably couple to said recess.

5. The carriage assembly of claim 4, wherein said jaw configured to operably couple to said recess further comprises prohibiting rotational displacement of said jaw when said threaded rod is advanced.

* * * * *